US011904186B2

(12) United States Patent
Jin et al.

(10) Patent No.: US 11,904,186 B2
(45) Date of Patent: Feb. 20, 2024

(54) RADIOTHERAPEUTICAL OR RADIOSURGICAL SYSTEM COMPRISING TWO OR MORE ROTATABLE HIGH-INTENSITY RADIATION SOURCES AND A RING-SHAPED IMAGER, AND METHODS THEREOF

(71) Applicants: Jianyue Jin, Waite Hill, OH (US); Fengming Kong, Waite Hill, OH (US)

(72) Inventors: Jianyue Jin, Waite Hill, OH (US); Fengming Kong, Waite Hill, OH (US)

(73) Assignees: Capital Medical University, Beijing (CN); The University of Hong Kong—Shenzhen Hospital, Shenzhen (CN)

( * ) Notice: Subject to any disclaimer, the term of this patent is extended or adjusted under 35 U.S.C. 154(b) by 60 days.

(21) Appl. No.: 17/647,848

(22) Filed: Jan. 12, 2022

(65) Prior Publication Data
US 2023/0218929 A1  Jul. 13, 2023

(51) Int. Cl.
*A61N 5/10*  (2006.01)

(52) U.S. Cl.
CPC ........... *A61N 5/1081* (2013.01); *A61N 5/103* (2013.01); *A61N 5/1039* (2013.01); *A61N 5/1045* (2013.01); *A61N 5/1049* (2013.01); *A61N 5/1067* (2013.01); *A61N 5/1084* (2013.01); *A61N 2005/1052* (2013.01); *A61N 2005/1055* (2013.01); *A61N 2005/1061* (2013.01)

(58) Field of Classification Search
CPC ........ A61N 5/10; A61N 5/103; A61N 5/1039; A61N 5/1042; A61N 5/1045; A61N 5/1047; A61N 5/1048; A61N 5/1049; A61N 2005/1052; A61N 2005/1055; A61N 2005/1061; A61N 5/1067; A61N 5/1077; A61N 5/1081; A61N 5/1082
USPC .......................................................... 378/65
See application file for complete search history.

(56) References Cited

U.S. PATENT DOCUMENTS

| 6,535,574 B1 * | 3/2003 | Collins ................ A61N 5/1049 |
| | | 378/65 |
| 6,560,311 B1 * | 5/2003 | Shepard ............... A61N 5/1031 |
| | | 378/65 |

(Continued)

*Primary Examiner* — Allen C. Ho
(74) *Attorney, Agent, or Firm* — George Guosheng Wang; Upstream Research and Patent LLC

(57) ABSTRACT

The invention provides a radiotherapeutical or radiosurgical system comprising at least two high-intensity radiation sources configured to rotate around a common rotation axis and a ring-shaped imaging device. A three-source configuration is considered as the most cost-effective and will be used as an example for illustration. The configuration of these high-intensity radiation sources and use of a unique compact MLC for each of the radiation sources make it possible for the system to rapidly deliver high-conformal non-coplanar stereotactic radiation treatment in one gantry rotation without any couch rotation. Therefore the invention can deliver high precision and high-conformal non-coplanar stereotactic radiation treatment to any part of the body in an extremely short time (0.1-20 seconds), which may exhibit numerous advantages over the prior art, such as reduction of radiation damage to the circulating immune cells in blood and mitigation of patient motion-induced problems, among others.

18 Claims, 13 Drawing Sheets

(56) References Cited

U.S. PATENT DOCUMENTS

| | | | | |
|---|---|---|---|---|
| 7,227,925 | B1 * | 6/2007 | Mansfield | A61N 5/1049 378/65 |
| 7,623,623 | B2 * | 11/2009 | Raanes | A61B 6/4458 378/68 |
| 7,729,472 | B2 * | 6/2010 | Scherch | A61N 5/1049 378/65 |
| 7,856,082 | B2 * | 12/2010 | Flynn | A61N 5/103 378/65 |
| 7,906,770 | B2 * | 3/2011 | Otto | A61N 5/1047 378/65 |
| 7,945,021 | B2 * | 5/2011 | Shapiro | A61N 5/1048 378/65 |
| 8,519,370 | B2 * | 8/2013 | Luzzara | A61N 5/1045 250/492.1 |
| 8,536,547 | B2 * | 9/2013 | Maurer, Jr. | A61B 6/4447 250/492.1 |
| 8,613,694 | B2 * | 12/2013 | Walsh | A61N 5/103 378/65 |
| 8,861,672 | B2 * | 10/2014 | Maltz | A61B 6/5223 378/65 |
| 8,917,813 | B2 * | 12/2014 | Maurer, Jr. | A61N 5/1065 378/65 |
| 8,934,605 | B2 * | 1/2015 | Maurer, Jr. | A61N 5/1048 378/65 |
| 8,989,846 | B2 * | 3/2015 | Kuduvalli | A61B 6/4476 600/407 |
| 9,289,627 | B2 * | 3/2016 | Otto | G01T 1/29 |
| 9,498,167 | B2 * | 11/2016 | Mostafavi | A61N 5/10 |
| 9,652,871 | B2 * | 5/2017 | Han | G06T 11/003 |
| 9,687,200 | B2 * | 6/2017 | Maurer, Jr. | A61B 6/032 |
| 10,143,859 | B2 * | 12/2018 | Ollila | A61N 5/1031 |
| 10,406,382 | B2 * | 9/2019 | Humber | A61B 6/4085 |
| 10,688,320 | B2 * | 6/2020 | Voronenko | A61N 5/1036 |
| 10,751,014 | B2 * | 8/2020 | Naylor | A61N 5/1067 |
| 10,828,514 | B2 * | 11/2020 | Kleven | A61N 5/1067 |
| 11,000,706 | B2 * | 5/2021 | Kawrykow | A61N 5/1049 |
| 11,040,221 | B2 * | 6/2021 | Lachaine | G16H 20/40 |
| 11,504,550 | B2 * | 11/2022 | Maolinbay | A61B 6/4085 |
| 11,654,300 | B2 * | 5/2023 | Olcott | A61N 5/1038 378/65 |

\* cited by examiner (Side View)

(Front View)
100

RADIOTHERAPEUTICAL OR RADIOSURGICAL SYSTEM COMPRISING TWO OR MORE ROTATABLE HIGH-INTENSITY RADIATION SOURCES AND A RING-SHAPED IMAGER, AND METHODS THEREOF

CROSS-REFERENCE TO RELATED APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

FIELD OF THE INVENTION

The present invention generally relates to the field of radiotherapeutical or radiosurgical technology. The invention includes a radiotherapeutical or radiosurgical system comprising two or more rotatable high-intensity radiation sources and a ring-shaped imager, and methods thereof. The two or more high-intensity radiation sources in the invention will be generally illustrated, explained and exemplified by three linear accelerators (LINACS), because a LINAC is one of the preferred choices for the high-intensity radiation source due to its compact size and high radiation intensity, and the number of three radiation sources is one of the optimal choices for the balance of functionality (or efficiency) and cost. However, it should be appreciated that the number of radiation sources can be two, three, four or more; and the radiation sources can also be any other types of radiation sources, for example, isotopes emitting high intensity radiation, x-rays and other particles generated by any other compact accelerators, and the like.

BACKGROUND OF THE INVENTION

Radiation therapy or radiotherapy works by damaging the DNA of target cells such as cancerous cells. The DNA damage may be caused by either direct or indirect ionization of the DNA atoms. Indirect ionization of DNA atoms involves the ionization of non-DNA atoms such as water, forming free radicals such as hydroxyl radicals that damage the DNA. For example, most of the radiation effect in photon therapy is through free radicals.

Types of radiation therapy include external beam radiation therapy (EBRT or XRT) or teletherapy (including particle therapy using protons or heavier ions); brachytherapy or sealed source radiation therapy; systemic radioisotope therapy or unsealed source radiotherapy; radionuclide therapy; and intraoperative radiotherapy. During a process of EBRT, the patient lies or sits on a couch and an external source of ionizing radiation is pointed at a particular part of the body. Megavoltage X-rays are used to treat deep-seated tumors (e.g. bladder, bowel, prostate, lung, or brain), while orthovoltage X-rays are used for treating skin cancer and superficial structures. In contrast, megavoltage electron beams are typically used to treat superficial lesions extending to a depth of approximately 5 cm (increasing beam energy corresponds to greater penetration). Beams of heavier particles, particularly protons, may also be used in EBRT owing to their rapid drop-off in absorbed dose beneath the depth of the target.

Intensity modulated radiotherapy (IMRT) is often used in Megavoltage X-ray based EBRT to spare critical organs (organs at risk) while maintain sufficient radiation dose to the target. A multileave collimator (MLC), which consists of two banks (sets) of metal leaflets that can be moved to shape the radiation field, or be moved within the radiation field to block the radiation to the critical organ, is usually incorporated with a complicated inverse treatment planning system to calculate the optimal leave move patterns to achieve the IMRT goal. The MLC leave are required to travel from one edge to the opposite edge of a radiation field. The leave length of both banks should be slightly longer than the opening of the radiation field.

Image-guided radiation therapy (IGRT) is frequently used to accurately position the patient immediately prior to a treatment session, or to check the position during a treatment session by imaging the patient in the treatment room in the treatment position, and performing image registration or image comparison with the reference imaging from treatment planning. Imaging techniques for IGRT may include fluoroscopy, digital X-ray, computed tomography (CT), cone beam CT, MVCT, optical tracking, Mill, ultrasound, PET, and electromagnetic transponders, among others. IGRT can greatly improve the precision of radiotherapy.

However, the current available imagers for diagnostic radiology, such as CT, Mill and PET are mostly ring-shaped. The ring-shaped structure limits the treatment couch to rotate within the ring, and hence cannot deliver non-coplanar stereotactic treatment to the patients. The current available MRI-LINAC such as Unity (Elekta) and Mridian (Viewray), and PET/CT integrated LINAC such as Reflexion (Reflexion medical) use a single LINAC based ring-shaped design for the treatment unit. However, because the couch cannot rotate within the ring, the radiation is only delivered in a coplanar manner. The dose distribution to the target is not as good as the non-coplanar stereotactic radiation treatment provided by stereotactic treatment units such as Gamma Knife and Zap-X. While the Gamma Knife and ZAP-X can provide non-coplanar stereotactic treatment, they are only limited to treat lesions in the cranial region, and no imager is integrated in the unit. In addition, both Gamma Knife and ZAP-X use circular collimator to define the radiation field. Multiple shots have to be used to cover the irregular target, so that the delivery time can be extended to 30-60 minutes for one large lesion.

Advantageously, the radiotherapeutical or radiosurgical system of the present invention can provide non-coplanar stereotactic radiation delivery with a ring-shaped structure and overcome the problems in the prior art. In some embodiments, the radiotherapeutical or radiosurgical system of the present invention uses a special design of multiple high-intensity radiation sources and a compact MLC for each source to overcome the problems in the prior art. In addition, the use of multiple high-intensity radiation sources in the radiotherapeutical or radiosurgical system of the present invention makes it possible to deliver the treatment in a few seconds, which can mitigate some motion-induced problems, and improve the radiotherapeutical efficiency.

SUMMARY OF THE INVENTION

One aspect of the present invention provides a radiotherapeutical or radiosurgical system comprising at least two radiation sources (preferably at least three radiation sources, and more preferably only three radiation sources) configured to rotate around a common rotation axis and target at a common point on the rotation axis. The common point on the rotation axis is defined as an isocenter, and a predetermined treatment target is located at the isocenter. In exemplary embodiments that use three or more radiation sources, a first radiation source emits a first radiation beam which irradiates upon the predetermined treatment target from a first direction (e.g. a central axis of the first radiation beam), and a first angle $\alpha 1$ is defined as the angle between the first direction and the common rotation axis. A second radiation source emits a second radiation beam which irradiates upon the predetermined treatment target from a second direction (e.g. a central axis of the second radiation beam), and a second angle $\alpha 2$ is defined as the angle between the second direction and the common rotation axis. A third radiation source emits a third radiation beam which irradiates upon the predetermined treatment target from a third direction (e.g. a central axis of the third radiation beam), and a third angle $\alpha 3$ is defined as the angle between the third direction and the common rotation axis. When the at least three radiation sources are rotating around the common rotation axis (e.g. during a radiation treatment), the angles $\alpha 1$, $\alpha 2$ and $\alpha 3$ are independently of each other constant or variable with a magnitude of less than $\pm 15°$. When the at least three radiation sources are rotating around the common rotation axis (e.g. during a radiation treatment), it always remains that $\alpha 1 \neq \alpha 2$, $\alpha 1 \neq \alpha 3$, and $\alpha 2 \neq \alpha 3$, regardless the angles $\alpha 1$, $\alpha 2$ and $\alpha 3$ are constant or variable.

In some embodiments, the at least two radiation sources are high-intensity radiation sources. The term "high-intensity" is usually defined here as a dose-rate of at least 20 Gy/minute, at 100 cm source to target distance. High dose-rate is required to achieve maximum delivery time of 20 seconds, especially for radiosurgical treatment. However, in certain situations, especially for radiotherapeutical treatment, a dose-rate of at least 3 Gy/minute at 100 cm source to target distance may also be acceptable. Therefore, a dose rate between 3-20 Gy/minute at 100 cm source to target distance is still defined as high-intensity.

In various embodiments, the special configuration of these high-intensity radiation sources and use of a unique compact MLC for each of the radiation sources make it possible for the system to rapidly deliver high-conformal non-coplanar stereotactic radiation treatment in one gantry rotation without any couch rotation. Consequently, a ring-shaped imaging device, which does not allow couch rotation, can be integrated into the system to provide high-precision image guidance. Therefore, the present invention can deliver high precision and high-conformal non-coplanar stereotactic radiation treatment to any part of the body in an extremely short time (0.1-20 seconds), which may exhibit numerous advantages over the prior art, such as reduction of radiation damage to the circulating immune cells in blood and mitigation of patient motion-induced problems, among others.

Another aspect of the invention provides a method of radiotherapeutical or radiosurgical treatment. The method includes at least the following steps: (i) providing the system as described above; (ii) providing a system of treatment planning; the treatment target (such as a tumor) is contoured in a 3-dimensional (3D) imaging set (such as CT imaging set), and the dose rate and the collimator shape of each radiation source at each rotation angle (e.g. every 5-10°) in 360° rotation are determined according to the dose prescription and the target shape in each beam's eye view; (iii) positioning the patient according to the 3D imaging as provided by a ring-shaped imaging device, so that the target is in exactly the same position as that in the 3D imaging in the treatment planning system; and (iv) delivering a prescription radiation dose to the predetermined target according to the treatment plan and completing the treatment within 0.1-20 seconds in a full 360° rotation, a partial rotation with any angles less than 360°, or no rotation.

In some embodiments, the radiotherapeutical or radiosurgical system delivers non-coplanar stereotactic radiation treatment in a very short time (0.1-20 seconds) precisely to a predetermined target in any parts of the body according to the imaging taken right before radiation delivery.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

Figure 1:
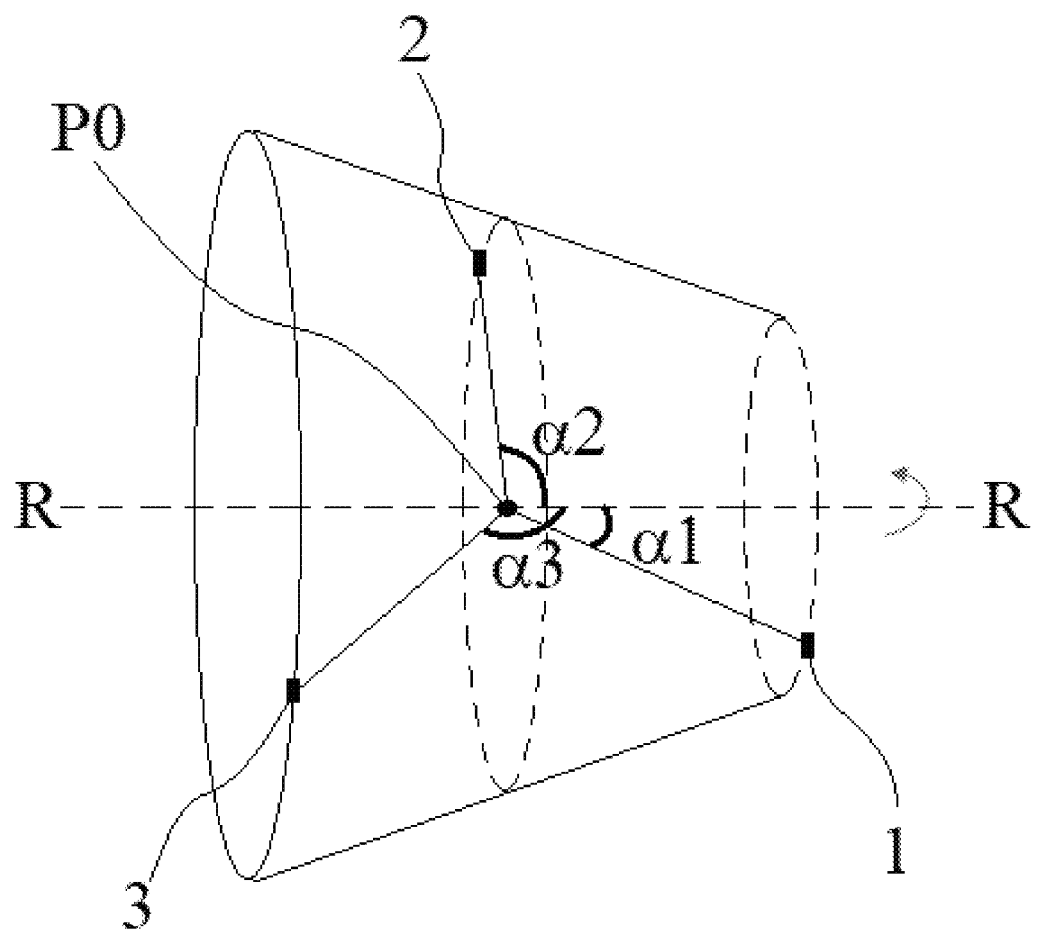
FIG. 1 schematically illustrates a general radiotherapeutical or radiosurgical system in accordance with an exemplary embodiment of the present invention.

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

It is also to be understood that the terminology used herein is for the purpose of describing particular embodiments only, and is not intended to limit the scope of the invention. For example, when an element is referred to as being "on", "connected to", or "coupled to" another element, it can be directly on, connected or coupled to the other element or intervening elements may be present. In contrast, when an element is referred to as being "directly on", "directly connected to", or "directly coupled to" another element, there are no intervening elements present.

Throughout the specification and claims, the following terms take the meanings explicitly associated herein, unless the context clearly dictates otherwise. The phrase "in one embodiment" does not necessarily refer to the same embodiment, although it may. Furthermore, the phrase "in another embodiment" does not necessarily refer to a different embodiment, although it may. Thus, as described below, various embodiments of the invention may be readily combined without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

The present invention is useful in any suitable radiotherapeutical or radiosurgical fields. LINAC is the most suitable radiation source that can be used for the high-intensity radiation sources in this invention due to its compact size and capability of generating high intensity radiation; however, any types of radiation sources that have a compact size and generate high-intensity radiation can be used in the invention. A LINAC produces x-rays from the impact of accelerated electrons striking a high z target such as tungsten. The emission head or gantry can be mechanically rotated around a rotational axis. A table ("couch") where the patient is lying is placed with its longitudinal direction parallel to the gantry rotation axis. The table can be moved in small linear steps in 3 orthogonal directions to adjust patient position. The table may also be rotatable if the accelerator-based treatment unit is a C-shaped structure. The gantry can be stopped in a gantry position marked by the rotation angle (so that it often called gantry angle), and deliver radiation at this gantry angle. The radiation usually expands in certain size and shape when reach to the patient, and we usually called this radiation a radiation field. The radiation field size and shape are usually defined by a MLC, which forms an opening conforming to the target mass. A radiotherapy treatment usually consists of several radiation fields at different gantry positions. Usually, the more the radiation fields, the better the dose distribution to the target.

Radiation can also be delivered when gantry is rotating. This type of treatment approach is called arc. For arc treatment, a 3-5° span of gantry rotation can be approximately considered as a new radiation field, so a 360° arc may be equivalent to 120-72 radiation fields.

With reference to FIG. 1, a radiotherapeutical or radiosurgical system 100 includes three radiation sources (1, 2 and 3) as an exemplary embodiment. These radiation sources are configured to rotate around a common rotation axis R and target at a common point P0 on the rotation axis. The common point P0 on the rotation axis R may be defined as the isocenter as known to a skilled artisan in the field of radiotherapy or radiosurgery.

Referring again to FIG. 1, a predetermined treatment target such as a tumor is located at or around the isocenter P0. When the gantries (or rotation structure) are in e.g. the initial non-rotating position, a first radiation source 1 emits a first radiation beam which irradiates upon the predetermined treatment target from a first direction (e.g. a central axis of the first radiation beam), and a first angle $\alpha 1$ is defined as the angle between the first direction and the common rotation axis R. A second radiation source 2 emits a second radiation beam which irradiates upon the predetermined treatment target from a second direction (e.g. a central axis of the second radiation beam), and a second angle $\alpha 2$ is defined as the angle between the second direction and the common rotation axis R. A third radiation source 3 emits a third radiation beam which irradiates upon the predetermined treatment target from a third direction (e.g. a central axis of the third radiation beam), and a third angle $\alpha 3$ is defined as the angle between the third direction and the common rotation axis R.

As an exemplary embodiment, when the three radiation sources (1, 2 and 3) are rotating around the common rotation axis (for example, beam-on during a radiotherapeutical or radiosurgical process on a patient), the angles $\alpha 1$, $\alpha 2$ and $\alpha 3$ are independently of each other constant or variable with a magnitude of less than ±15°, as detailed in Table 1 below:

TABLE 1

| Settings | α1 | α2 | α3 |
| --- | --- | --- | --- |
| 1 | Constant | Constant | Constant |
| 2 | Variable | Constant | Constant |
| 3 | Constant | Variable | Constant |
| 4 | Constant | Constant | Variable |
| 5 | Constant | Variable | Variable |
| 6 | Variable | Constant | Variable |
| 7 | Variable | Variable | Constant |
| 8 | Variable | Variable | Variable |

In some embodiments of the invention, when the three radiation sources (1, 2 and 3) (or any number of radiation sources equal to or more than 2) are rotating around the common rotation axis R, the angles α1, α2 and α3 are independently of each other constant or variable with a magnitude of less than ±10°, less than ±5°, or less than ±2°.

However, when the three radiation sources (1, 2 and 3) in beam-on state are rotating around the common rotation axis R, it always remains that α1≠α2, α1≠α3, and α2≠α3, regardless the angles α1, α2 and α3 are constant or variable. In other words, when the three radiation sources (1, 2 and 3) in beam-on state are rotating around the common rotation axis R, it always remains that α1≠α2, α1≠α3, and α2≠α3 in all settings 1-8, as listed in Table 1.

For example, before a patient starts his or her beam-on radiotherapeutical or radiosurgical process, the three radiation sources (1, 2 and 3) in beam-off state do not have to rotate around the common rotation axis R. Such pre-treatment initial values of the angles (α1, α2 and α3) can be set at any suitable values. These pre-treatment initial values can be adjusted for an individual patient before the three radiation sources start to rotate around the common rotation axis, or before the beam-on radiotherapeutical or radiosurgical process. For example, the pre-treatment initial value of α1 may be 45° for patient X, but 42° for patient Y. Once a patient (e.g. patient X) starts his or her beam-on radiotherapeutical or radiosurgical process and the three radiation sources (1, 2 and 3) start to rotate around the common rotation axis R, α1 will remain constant like α1=45° or α1 will be variable with a magnitude of less than ±15° for patient X, that is, α1 will be varied within a range like (45+15)°≥α1≥(45-15°), i.e. 60°≥α1≥30°. By the same token, α1 can remain constant like α1=45° during the beam-on treatment; or it can be varied within smaller ranges if desired, such as 55°≥α1≥35°, 50°≥α1≥40°, or 47°≥α1≥43° during the beam-on treatment.

In various exemplary embodiments of the invention, the pre-treatment initial value of α1 may be in the range of 30-75°, the pre-treatment initial value of α2 may be in the range of 75-105°, and the pre-treatment initial value of α3 may be in the range of 105-150°, before the beam-on treatment, i.e. before the three radiation sources (1, 2 and 3) start to rotate around the common rotation axis R.

Figure 2:
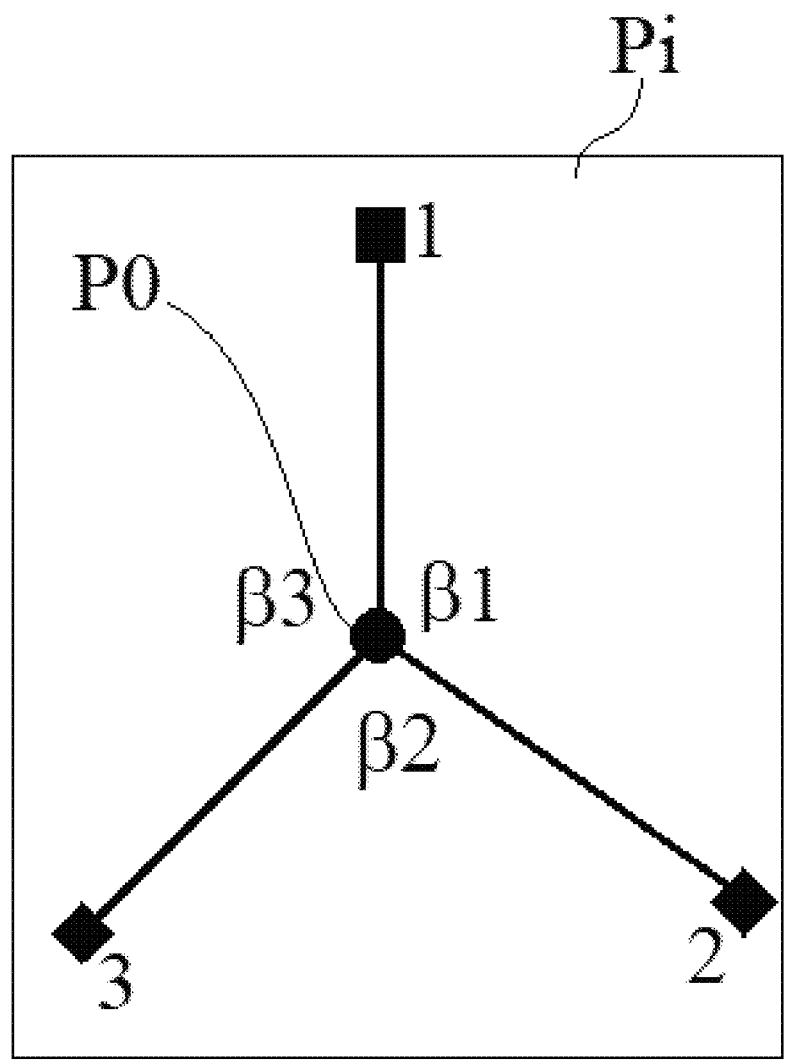
FIG. 2 illustrates the projection of radiation sources onto a plane passing through the isocenter and perpendicular to the common rotation axis in accordance with an exemplary embodiment of the present invention.

Referring to FIG. 2, each of the three radiation sources (1, 2 and 3) may conceptually project onto a plane Pi passing through the isocenter P0 and perpendicular to the common rotation axis R. The line connecting the source projection to the isocenter P0 is defined as the projection line of the corresponding radiation source. Specifically, angle β1 is defined as the angle between the projection line of the first radiation source 1 and the projection line of the second radiation source 2. Angle β2 is defined as the angle between the projection line of the second radiation source 2 and the projection line of the third radiation source 3. Angle β3 is defined as the angle between the projection line of the third radiation source 3 and the projection line of the first radiation source 1.

In various exemplary embodiments of the invention, β1, β2 and β3 are independently of each other in the range of 80-150° such as 100-140°. For example, when the radiotherapeutical or radiosurgical system of the invention includes only three radiation sources (1, 2 and 3), β1, β2 and β3 may be the same and β1=β2=β3=120°.

With the radiotherapeutical or radiosurgical system of the invention, the three radiation sources (1, 2 and 3) (or any number of radiation sources that are equal to or larger than two) are able to deliver 3 non-coplanar radiation fields to the treatment target without moving the gantry, and deliver 3 non-coplanar arcs in a single 360° rotation around the common axis R. The 3 non-coplanar arcs are equivalent to 360 non-coplanar stereotactic radiation fields (or beams) toward the isocenter, if a 3° span of rotation angle is considered as a different radiation field (or beam).

Figure 3:
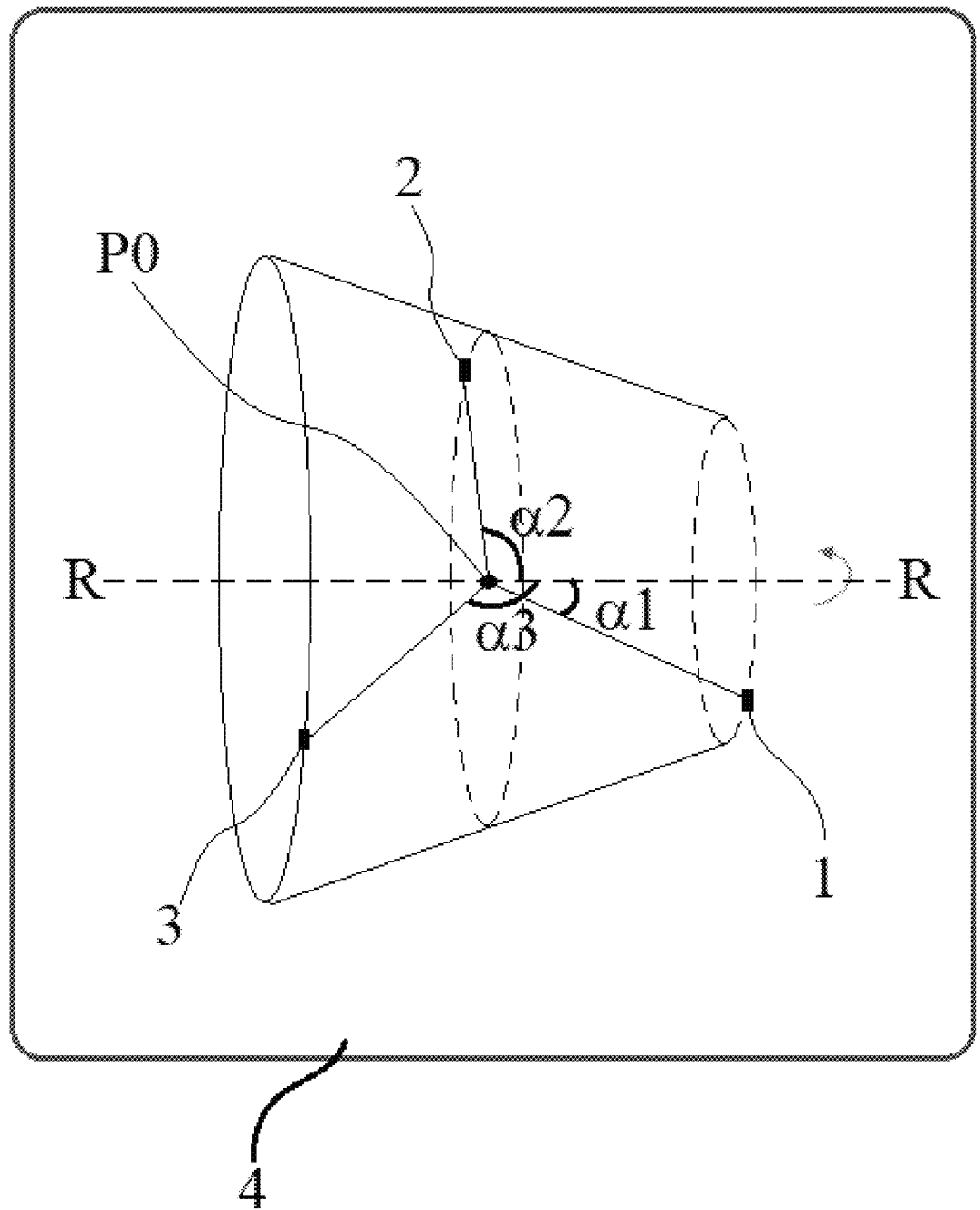
FIG. 3 schematically illustrates a treatment unit within a general radiotherapeutical or radiosurgical system in accordance with an exemplary embodiment of the present invention.
Figure 4:
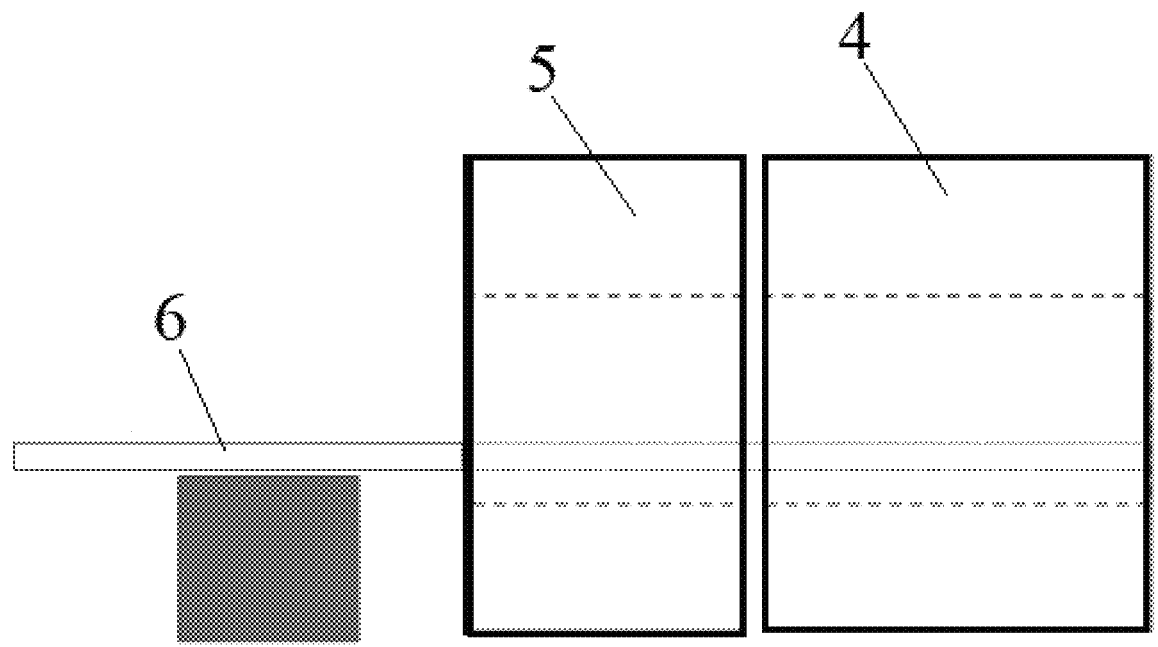
FIG. 4 schematically illustrates a ring-shaped imaging device and a treatment unit within a general radiotherapeutical or radiosurgical system in accordance with an exemplary embodiment of the present invention.
Figure 4:
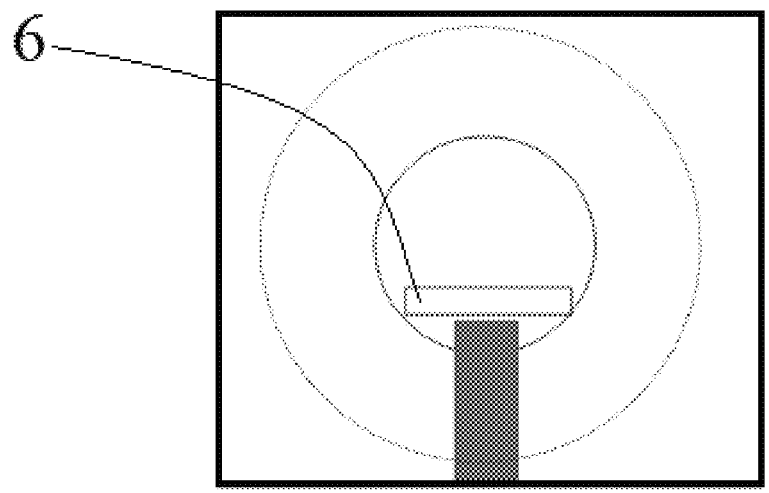

Referring to FIG. 3, the three radiation sources (1, 2 and 3) as described above may constitute a part of a treatment unit 4 within the radiotherapeutical or radiosurgical system 100. With reference to FIG. 4, the radiotherapeutical or radiosurgical system 100 may further include a ring-shaped imaging device 5 for guiding the radiation beams to focus on (or aim at) said predetermined treatment target. In some preferred embodiments, treatment unit 4 and ring-shaped imaging device 5 are arranged in a tandem configuration, and a patient can be smoothly moved from imaging device 5 into treatment unit 4 by moving the couch 6. Examples of the ring-shaped imaging devices include, but are not limited to, a CT, a MM, a PET, or any combinations thereof.

Figure 10:
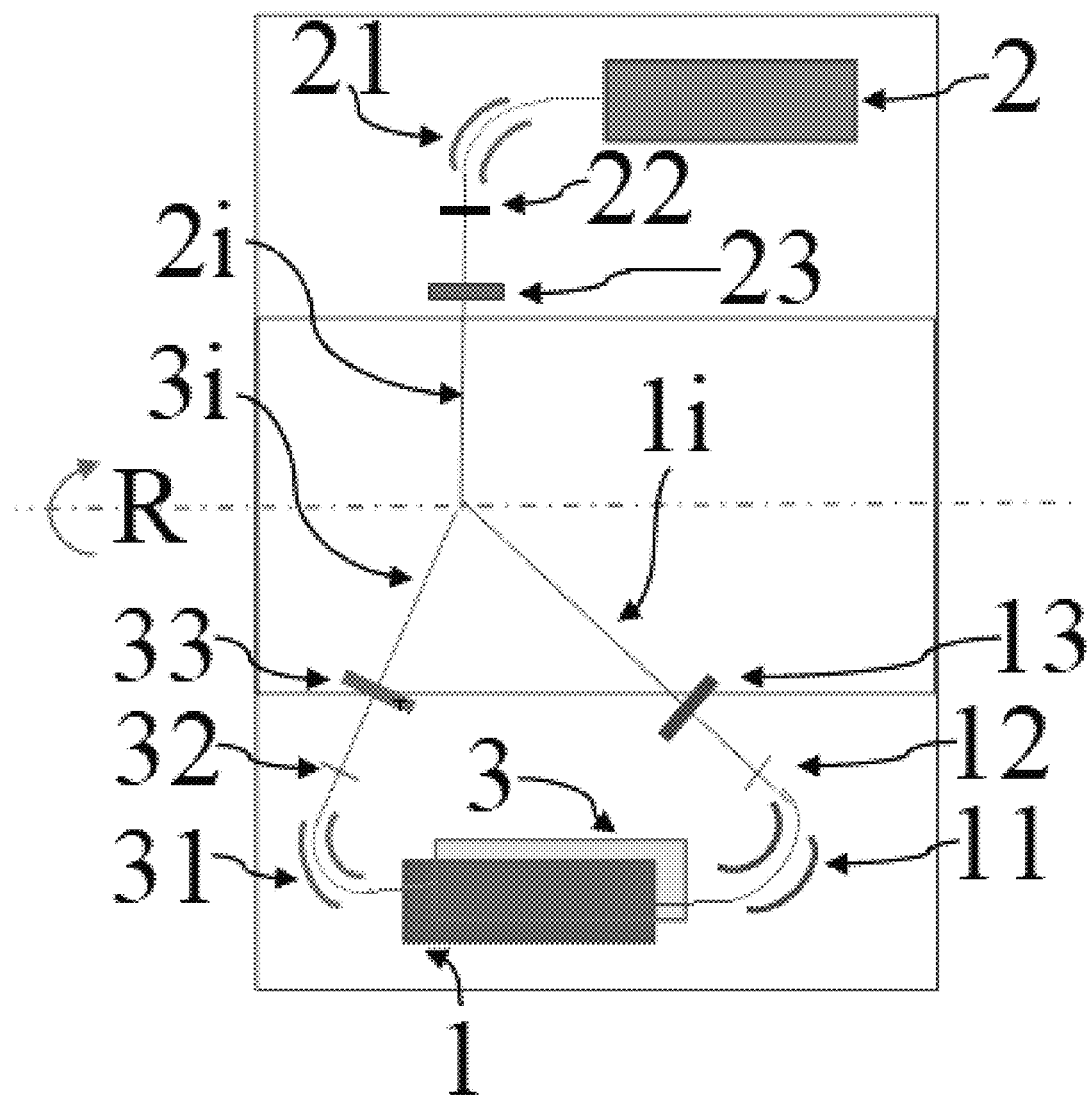
FIG. 10 schematically shows a side view of three linear accelerators with bending magnets in a general radiotherapeutical or radiosurgical system in accordance with an exemplary embodiment of the present invention.

In a variety of exemplary embodiments of the invention, the at least three radiation sources (1, 2, 3) are linear accelerators or other compact radiation sources that should have dose rate as high as possible to reduce treatment time (the minimum dose rate is 3 Gy/minute in 100 cm source-to-treatment-target distance, and a dose rate at least higher than 20 Gy/minute in 100 cm source-to-treatment target distance is preferable for each source). Usually, higher energy LINACs have higher dose rate and longer physical length (a LINAC generating 6 MV x-ray may achieve a dose rate of 15 Gy/minute in 100 cm source-to-treatment-target distance). In some embodiments, the linear accelerators (1, 2 and 3) have energy of <8 MeV, or the length of the accelerators is relatively short (for example, less than 40-80 cm). In such embodiments, bending magnets may not be needed to work with the LINACs (1, 2 and 3). The first, second and third directions as described above are the same as the axis of accelerator tubes of the LINACs (1, 2 and 3). In other embodiments as illustrated in FIG. 10, the LINACs (1, 2 and 3) have an energy of >8 MeV, or the length of the accelerator is relatively long (for example, longer than 40-80 cm). Bending magnets (11, 21 and 31) are needed to work with such LINACs (1, 2 and 3); and the first, second and third directions as described above are different from the axis of accelerator tubes of the LINACs (1, 2 and 3).

Figure 11:
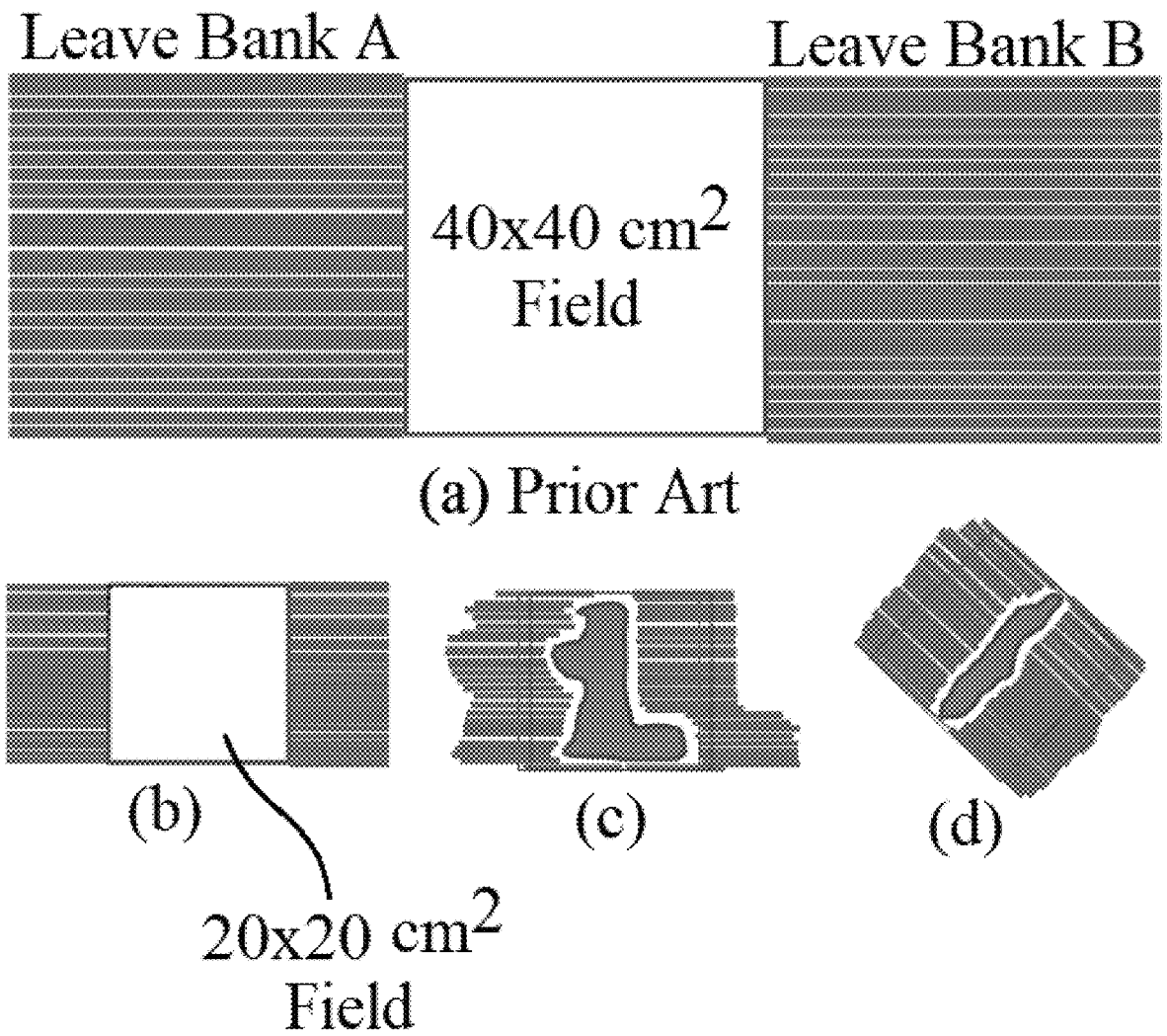
FIG. 11 shows the difference between a conventional MLC and a compact MLC designed for the radiotherapeutical or radiosurgical system in accordance with an exemplary embodiment of the present invention.

Preferred embodiments of the invention may spare normal tissues with shaped radiation beams aiming from various gantry angles during rotation. The radiotherapeutical or radiosurgical system of the invention further includes a special compact MLC (13, 23 or 33) for each radiation source (1, 2 or 3) as illustrated in FIGS. 10-11. The function of this MLC is to shape and reshape the radiation field to conform to the target shape in the beam's eye view during gantry rotation because the target shape in the beam's eye view changes with different beam directions. To achieve this goal, each leave of the MLC only needs to travel to a center of a field (instead of traveling all the way to the other edge of an opening when the MLC is used for IMRT). As such, the leave length and the overall dimension of the MLC are reduced, and consequently the dimension of treatment unit 4 is reduced as well.

In preferred embodiments of the invention, the LINACs in the radiotherapeutical or radiosurgical system can be modulated for their radiation output or dose rate during radiation delivery. For example, the dose rate from a LINAC (1, 2 or 3) may be temporarily reduced to 0-90% of its standard (or initial, or normal, or typical) dose rate when the gantry rotates around the common rotation axis R to a certain degree where a critical organ under protection from radiation is seen or detected from beam's eye view. Such intensity or dose rate modulation allows reduction of radiation dose to a critical (but vulnerable) bio-structure in the patient to (or under) a satisfaction level or a required level. Such intensity or dose rate modulation can achieve the same goal as a MLC for IMRT.

Figure 5:
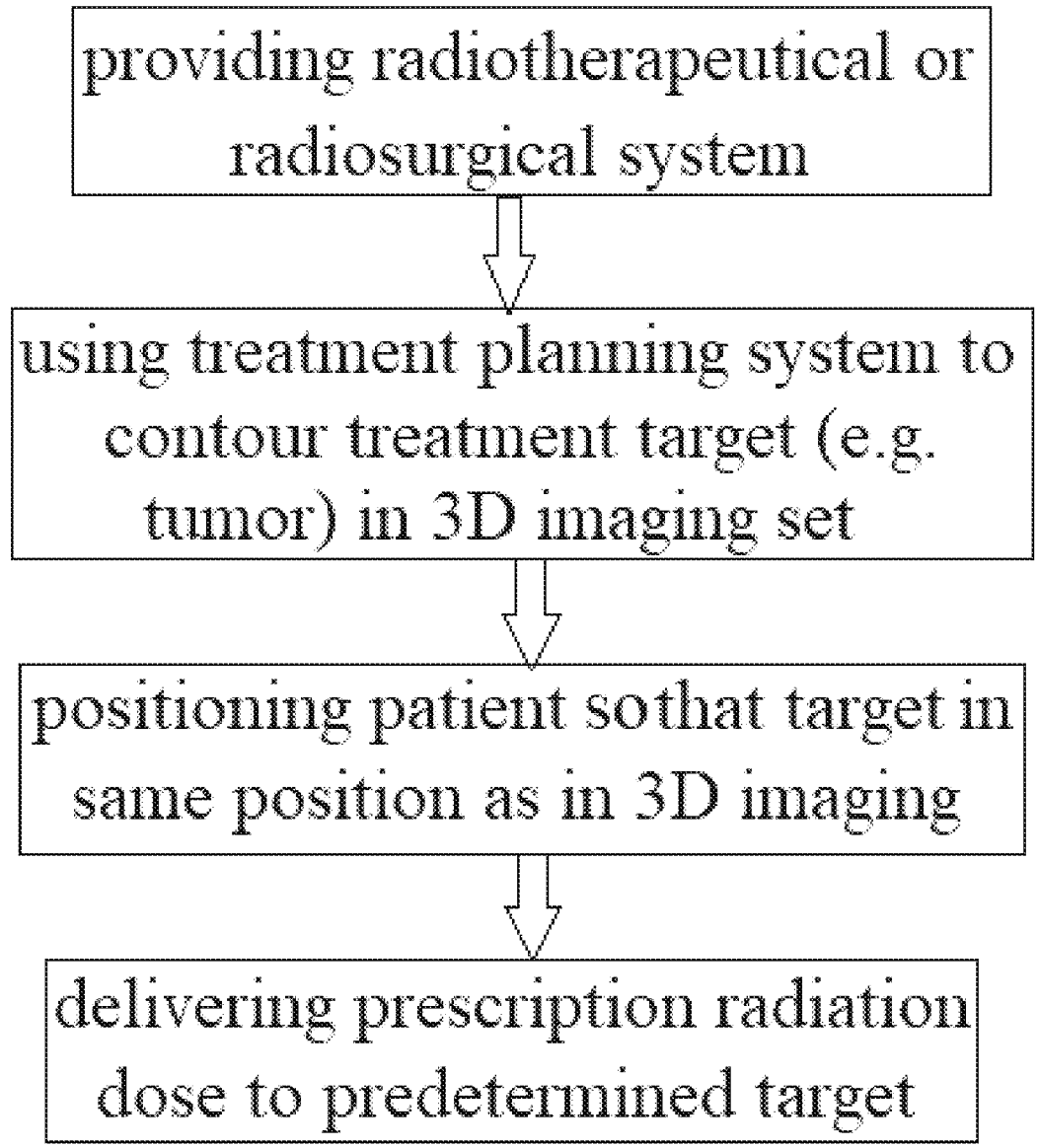
FIG. 5 depicts a flow chart of the radiotherapeutical or radiosurgical treatment method in accordance with an exemplary embodiment of the present invention.

Referring now to FIG. 5, the present invention provides a radiotherapeutical or radiosurgical treatment method that includes the following steps. Step (i) is providing the radiotherapeutical or radiosurgical system as described above. Step (ii) includes providing a system of treatment planning, and using the system to contour the treatment target (such as a tumor) in a 3-dimensional (3D) imaging set (such as CT imaging set). The treatment planning system uses a simple and fast forward planning algorithm to determine the dose rate and the collimator shape of each radiation source at each rotation angle (e.g. every 5-10°) in rotation of 360° according to the dose prescription and the target shape in each beam's eye view.

Step (iii) of the method includes positioning the patient according to the 3D imaging as provided by the ring-shaped imaging device 5 so that the target is in exactly the same position as that in the 3D imaging in the treatment planning system. A fast image registration algorithm may be used to assist the patient positioning. In step (iv), a prescription radiation dose is delivered to the predetermined target according to the treatment plan and the treatment is completed within 0.1-20 seconds in a full 360° rotation, a partial rotation with any angles less than 360°, or no rotation.

In typical embodiments, the radiotherapeutical or radiosurgical treatment method of the invention may further include a step of calculating the treatment delivery time or rotation time based on the maximal dose rate of each radiation source, maximal rotation speed and prescription dose. For example, if the maximal rotation speed is assumed to be limited to 4 second/rotation, and if the maximal dose rate is about 100 Gy/minute (using a >15 MeV LINAC), then the shortest treatment delivery time for 20 Gy prescription dose for a 3-source unit is 20/(100×3) minutes=4 seconds, corresponding to a full 360° rotation. When the prescription dose reduces to 2 Gy, the shortest treatment delivery time is only 0.4 seconds, corresponding to a 36° partial rotation with maximal rotation speed. Usually a full rotation results in a better dose distribution (better plan) than the partial rotation. However, in certainty situations, such as to mitigate the heart-beat induced target motion, a short treatment time is preferred. In such situations, a partial rotation or even no rotation treatment will be used to achieve minimal treatment time by sacrificing the dose distribution.

The radiotherapeutical or radiosurgical treatment method of the invention utilizes the multi-leave collimators (MLC) to conform the change of target shape during source rotation; and utilizes multiple high-intensity radiation sources to increase the dose rate. As a result, the present invention demonstrates a great advantage of reducing treatment delivery time to less than 20 seconds for any shapes and sizes of tumor, as compared to the conventional gamma knife (with multiple non-coplanar Co-60 radiation sources) and Zap-X devices which all use circular collimators and whose treatment delivery time is often more than 30 minutes for large tumors.

Moreover, the radiotherapeutical or radiosurgical treatment method of the present invention mitigates problems induced by patient's motions, including blood flow into the treatment volume. For example, when the treatment delivery time is less than 20 seconds, it substantially reduces the radiation dose to the immune cells in circulating blood and may reduce the potential radiation induced lymphopenia, because one cycle of blood circulation time is about 60 seconds. Radiation induced lymphopenia has been reported to be associated with poor survival for variety of tumors. When the treatment delivery time is less than 1 second, it is easy to mitigate the respiratory motion-induced target motion, considering a respiratory cycle is about 5 seconds and patient can hold the breath in about 10 seconds. When the treatment delivery time is less than 0.4 seconds, it may be able to mitigate the heart-beat induced target motion.

In various embodiments of the invention, LINACs are typically equipped with MLCs. A typical MLC consists of two sets of 40 to 80 leaves, each around 2.5 mm to 10 mm thick and several centimeters in the other two dimensions. Some MLCs have up to 160 leaves. Each leaf in the MLC is aligned parallel to the radiation field and can be moved independently to form an opening for the field shape, or block part of the field. Therefore, the MLCs have two functions: 1) shape the radiation fields, 2) perform IMRT to spare organs-at-risk (OARSs), while ensuring that the prescribed dose is delivered to the target(s). The leave only need to travel to the middle line if the MLC is only used for shaping the radiation field (first function), but the leave need to travel all the way to the opposite edge if the MLC is also used for IMRT (the second function).

In preferred embodiments of the invention, system 100 as shown in FIG. 1 includes a ring-shaped imaging-guided multi-source stereotactic radiotherapy device. A ring-shaped gantry structure with multiple radiation sources (three sources 1, 2 and 3 in FIG. 1) and a compact MLC for each source are used to delivery high precision non-coplanar stereotactic radiotherapy and/or radiosurgery to a target in any parts of a body. The ring-shaped structure allows the integration with any ring-shaped imaging devices such as CT, MRI, PET and SPECT for precise targeting. The special compact MLC design with leave not traveling beyond the middle line allows the housing of multiple radiation sources (1, 2, 3) in the ring structure while the MLC can still rapidly shape the field conforming to the target. The special multi-source design allows a single rotation to generate multiple non-coplanar arcs in a short time (as short as one second) for stereotactic radiation delivery. High dose-rate LINACs may preferably be used for the radiation sources (1, 2, 3). The rapid radiation delivery can not only greatly improve the efficiency, but also greatly reduce the patient motions during treatment. These motions include blood flow, respiratory motion, heartbeat and other physiology motion and physical motion.

Referring back to FIG. 4, the ring-shaped imager 5 can be easily integrated with ring-shaped treatment unit 4. The ring-shaped imager 5 could be a CT, a MM, a PET or the combination thereof, and it can provide accurate and precision anatomic and/or functional information of the target as well as other critical normal structures within the patient's body. However, the ring structure limits the treatment couch 6 rotation, so that radiation can only delivered in a co-planar manner. The present invention uses a multi-source treatment unit to overcome the problem.

Referring back to FIGS. 3 and 4, the treatment unit 4 is composed of multiple radiation sources (1, 2, 3) in configurations that one rotation of the ring structure can generate multiple (e.g. three) different non-coplanar arcs. The radiation sources (1, 2, 3) are usually LINACs that can generate high dose-rate x-rays. The number of sources could be any number equal or larger than 2. Use of n (n=2, 3, 4 . . . ) number of radiation sources can result in n number of non-coplanar arcs. Use of 3 sources (1, 2, 3) may be the most cost effective because the 3 arcs can achieve satisfactory non-coplanar stereotactic delivery. The stereotactic dose distribution may only have a limited improvement from 3 arcs to 4 arcs, but it may be greatly improved from 2 arcs to 3 arcs.

Figure 6:
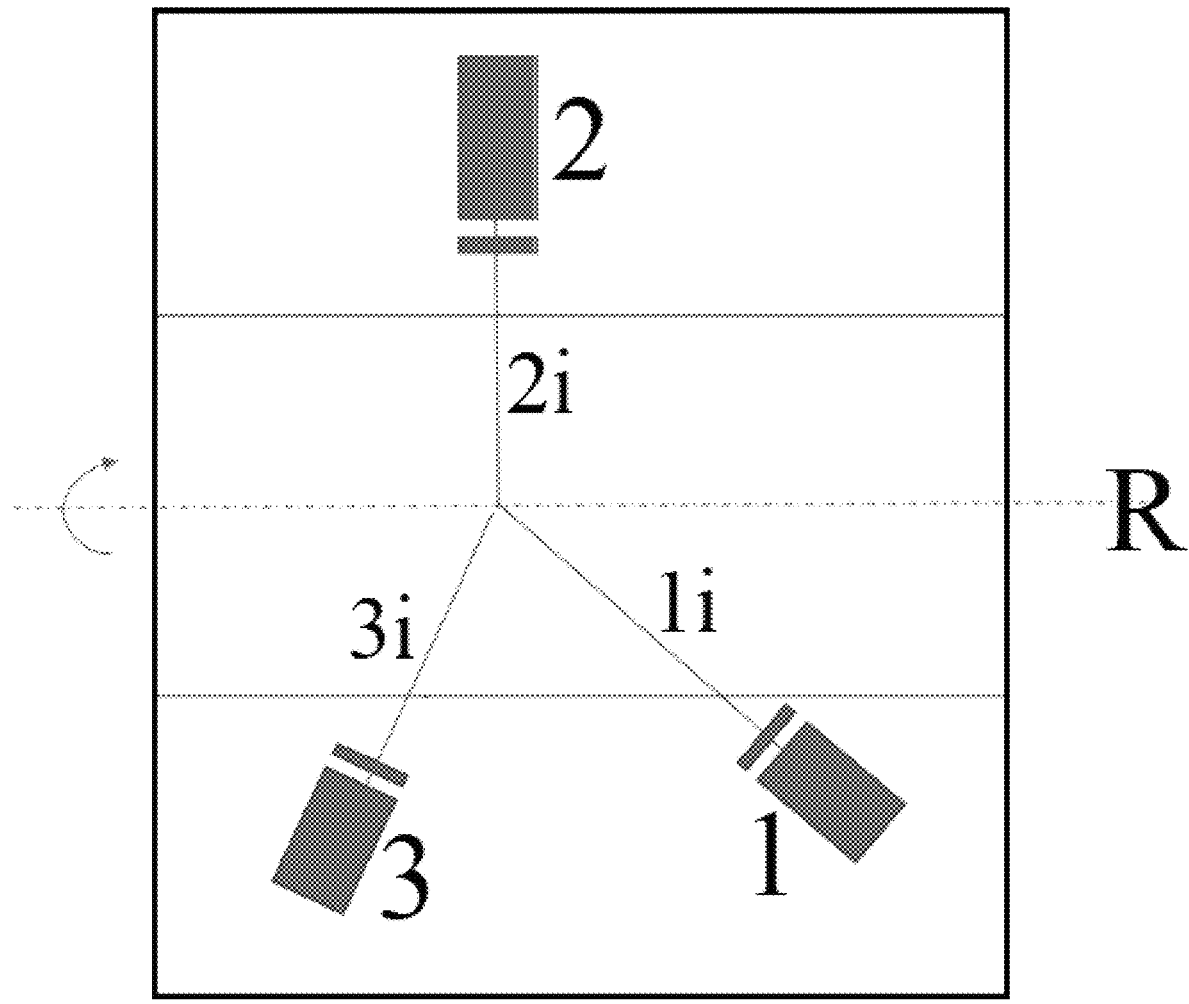
FIG. 6 schematically shows a side view of three linear accelerators without bending magnets in a general radiotherapeutical or radiosurgical system in accordance with an exemplary embodiment of the present invention.
Figure 7:
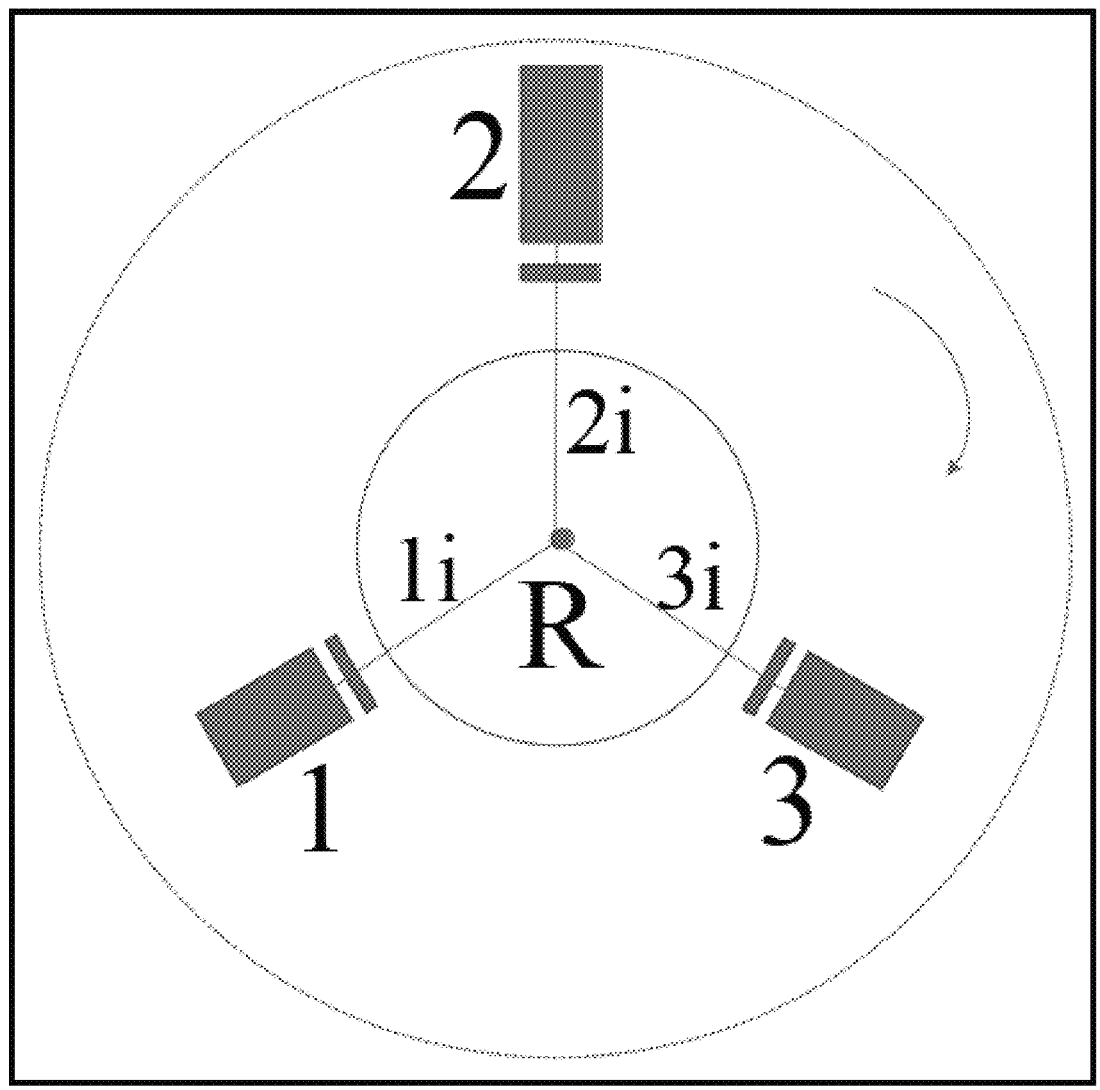
FIG. 7 schematically shows a front view of three linear accelerators without bending magnets in a general radiotherapeutical or radiosurgical system in accordance with an exemplary embodiment of the present invention.
Figure 8:
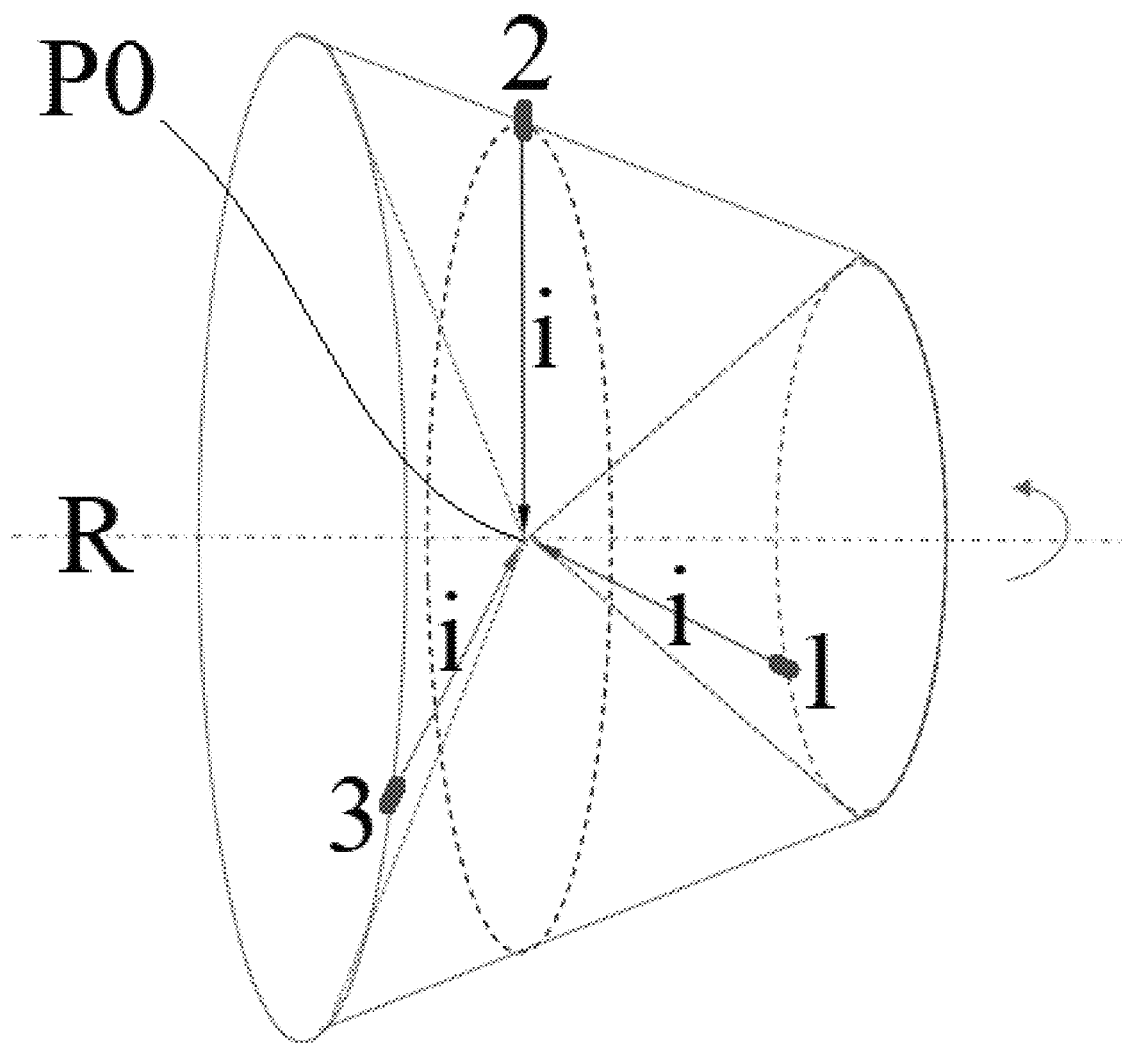
FIG. 8 schematically shows a 3D view inside a ring structure of a radiotherapeutical or radiosurgical system with three linear accelerators without bending magnets in accordance with an exemplary embodiment of the present invention.
Figure 9:
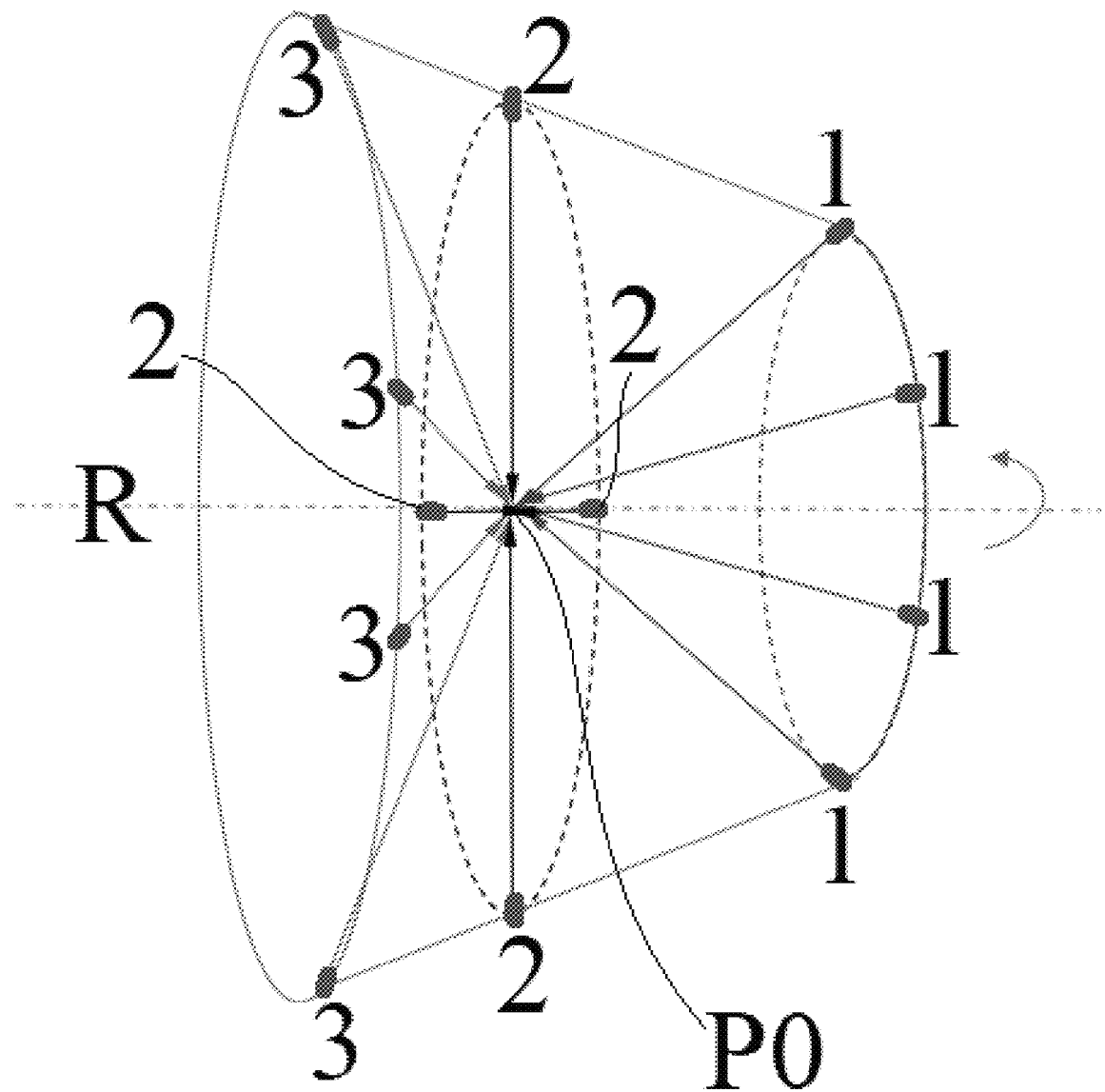
FIG. 9 shows a 360° rotation of the ring structure of a radiotherapeutical or radiosurgical system with three linear accelerators without bending magnets in accordance with an exemplary embodiment of the present invention.

When the length of accelerator is short (typically for energy less than 8 MeV), no bending magnets are needed, and the central beam axis is the same as the axis of the accelerator tube. FIGS. 6-9 show the diagram of an example of the 3-source configuration without bending magnets, in which FIG. 6 is the side view, FIG. 7 is the front view, and FIG. 8 is a 3D view inside the ring structure. With the 3-source configuration, a 360° rotation of the ring structure can generate 3 non-coplanar arcs of high stereotactic radiation delivery. FIG. 9 shows that a 360° rotation of the ring structure generates 3 arcs with each field in each arc focusing on the isocenter P0 from different directions. The central beam axis (1i, 2i and 3i; or simply i) of each of the 3 radiation sources (1, 2, 3) intercepts with the rotation axis R of the ring structure and forms 3 different angles $\alpha_1$, $\alpha_2$, and $\alpha_3$, respectively for the 3 sources, as shown in both FIG. 8 and FIG. 1. When $\alpha_1$, $\alpha_2$, and $\alpha_3$ are not equal to each other, the multiple radiation fields generated by each radiation source during a 360° rotation pass through different pathways and all focus on the isocenter (target) P0 to form non-coplanar stereotactic radiation delivery, as illustrated in FIG. 9. Considering each 5° as a different field, a 360° rotation for the 3 sources (1, 2, 3) can generate total of 72×3=216 fields from different directions focusing on the target P0. If 3° as a different fields, the total number of fields will be 360.

In some exemplary embodiments as illustrated in FIG. 10, the length of the high energy accelerator tube (such as >8 MeV) is usually quite long so that the diameter of the ring structure in treatment unit 4 have to be enlarged to house the accelerators (1, 2, 3). In such situations, the LINACs (1, 2, 3) can be placed with the axis of the accelerator tube parallel to the rotation axis R of the ring structure, and a bending magnet (11, 21, 31) can be used to change the central beam axis (1i, 2i, 3i) to a required direction. Subsequently, the beam passes through corresponding target (12, 22, 32) and corresponding multi-leave collimator (MLC 13, 23 or 33) before it irradiates on P0. When the accelerators (1, 2, 3) are placed in parallel with the rotation axis R, the same size ring structure in treatment unit 4 is sufficient to house much longer accelerators (1, 2, 3), and the bending magnets (11, 21, 31) are able to change the directions of central beam axis of the 3 radiation sources exactly same as that in FIGS. 6-9.

In contrast, the linear accelerators (LINACs) (1, 2, 3) in FIGS. 6-9 can be placed with the axis of the accelerator tube parallel to corresponding central beam axis (li, 2i, 3i). FIG. 10 illustrates the use of a bending magnet (11, 21, 31) to change the central beam axis to a desired direction. The 3 LINACs (1, 2, 3) are placed parallel to the rotation axis R so that their original radiation central axis is not able to intercept with the rotation axis R. The bending magnets (11, 21, 31) change the directions of the central axis into the direction exactly as that in FIGS. 6-9, so that the 3 central axes intercept with the rotation axis at the isocenter point P0.

In certain embodiments of the invention, the MLCs (13, 23, 33) as shown in FIG. 10 may have a compact design. A compact MLC design is preferably used to ensure that the ring structure is able to house multiple radiation sources. This invention may use two strategies to achieve a compact MLC design: 1) reduce maximum treatment field size, 2) only use the MLC for field shaping, not for IMRT. Because most of the tumor sizes are less than 15 cm, and the treatment unit 4 of the present invention may be mainly used for stereotactic radiotherapy/radiosurgery (SRT/SRS), the maximum treatment field can be reduced to 15 cm instead of the 40 cm in conventional radiotherapy. Using MLC only for shaping the field allows the MLC leave to only travel to the middle line of the fields, so that the leave length of both banks can be reduced by half in comparison to MLC for IMRT.

Refer to FIG. 11 for a comparison of the compact MLC with a conventional MLC. Panel (a) shows a conventional MLC with e.g. 40×40 cm$^2$ maximum field opening. The leave length for both leave banks A and B are slightly larger than 40 cm to avoid leak in the back end. Conventional MLC has the opening of 40×40 cm$^2$ to treat large volume and the leave can travel all the way from one edge of the opening to the other edge for intensity modulated radiotherapy (IMRT). Therefore, each leaf has to have a length of at least 40 cm (the maximum field opening), so that when the front end of the leaf travels to the far edge of the opening, the back end of the leaf can still cover the field to avoid leak. In such situation, the MLC dimension is equivalent to 120 cm in the isocenter position. The actual physical MLC dimension would be 60 cm if the MLC is placed halfway from the radiation source to the isocenter.

Panel (b) of FIG. 11 shows a compact MLC of the invention with e.g. 20×20 cm$^2$ maximum field opening. The leave only need to travel to the middle line (vertical line) of the field so that the leave length in both leave banks A and B is only slightly larger than 10 cm. Panels (c) and (d) of FIG. 11 show that the compact MLC (13, 23, 33) can shape the field conforming to irregular targets without causing leak in the back end. Therefore, even if we use a maximum field size of 20×20 cm$^2$, the MLC dimension would be 40 cm in the isocenter location, and a physical dimension of 20 cm if the MLC is placed halfway between the radiation source and the isocenter. This is a substantial dimension reduction in comparison to the 60 cm for conventional MLC. If the maximum field size is 15×15 cm$^2$, the physical MLC dimension is only 15 cm if the MLC is placed halfway between the source and isocenter.

Figure 12:
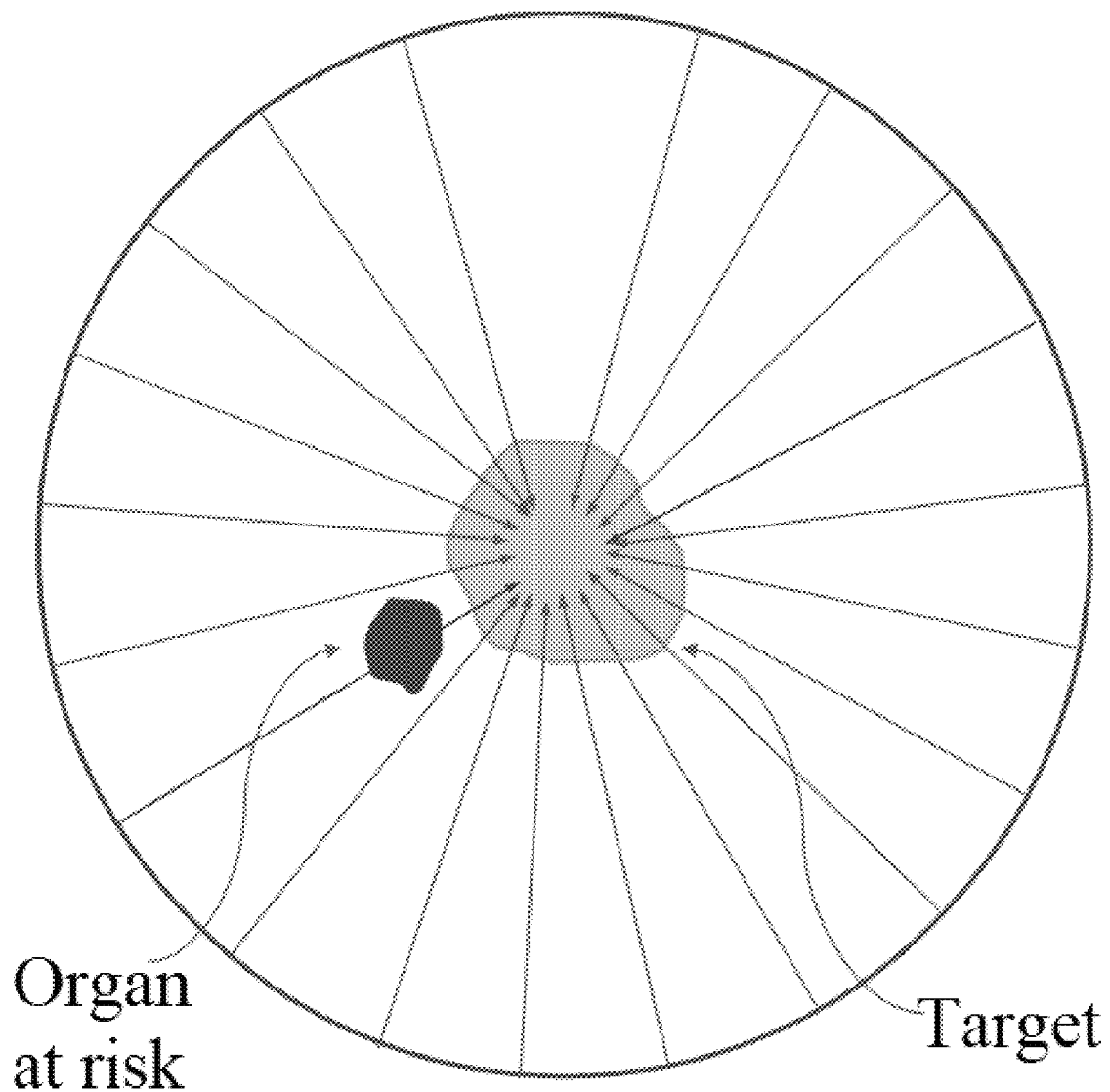
FIG. 12 is an illustration of IMRT by directly modulating dose output of the radiation sources during gantry rotation in accordance with an exemplary embodiment of the present invention.

Intensity modulated radiation therapy (IMRT) is an advanced radiotherapy technique used to minimize the amount of normal tissue being irradiated in the treatment field. With IMRT, doctors are often able to further limit the amount of radiation received by critical organs near the tumor. Doctors have found this sometimes allowed them to safely give a higher dose of radiation to the tumor, if desired. IMRT can be achieved by using a MLC. However, IMRT are usually not used for SRT and SRS because of their steep dose falloff by using multiple non-coplanar arcs or over 100 non-coplanar radiation beams. The use of a compact MLC has eliminated the MLC's IMRT capability in the present invention. However, many embodiments of the invention can still carry out IMRT by directly modulating the source output (dose rate) rather than use the MLC. FIG. 12 is an illustration of IMRT by directly modulating dose output of the radiation source during gantry rotation. The dose output for fields that may pass through an organ at risk may be reduced to a much lower level, or even to zero to reduce the dose to the organ at risk. Consequently, the radiation dose to the organ at risk is greatly reduced in comparison to that without the intensity modulation. This approach of IMRT is also much faster and more efficient than the MLC-based IMRT approach.

Figure 13:
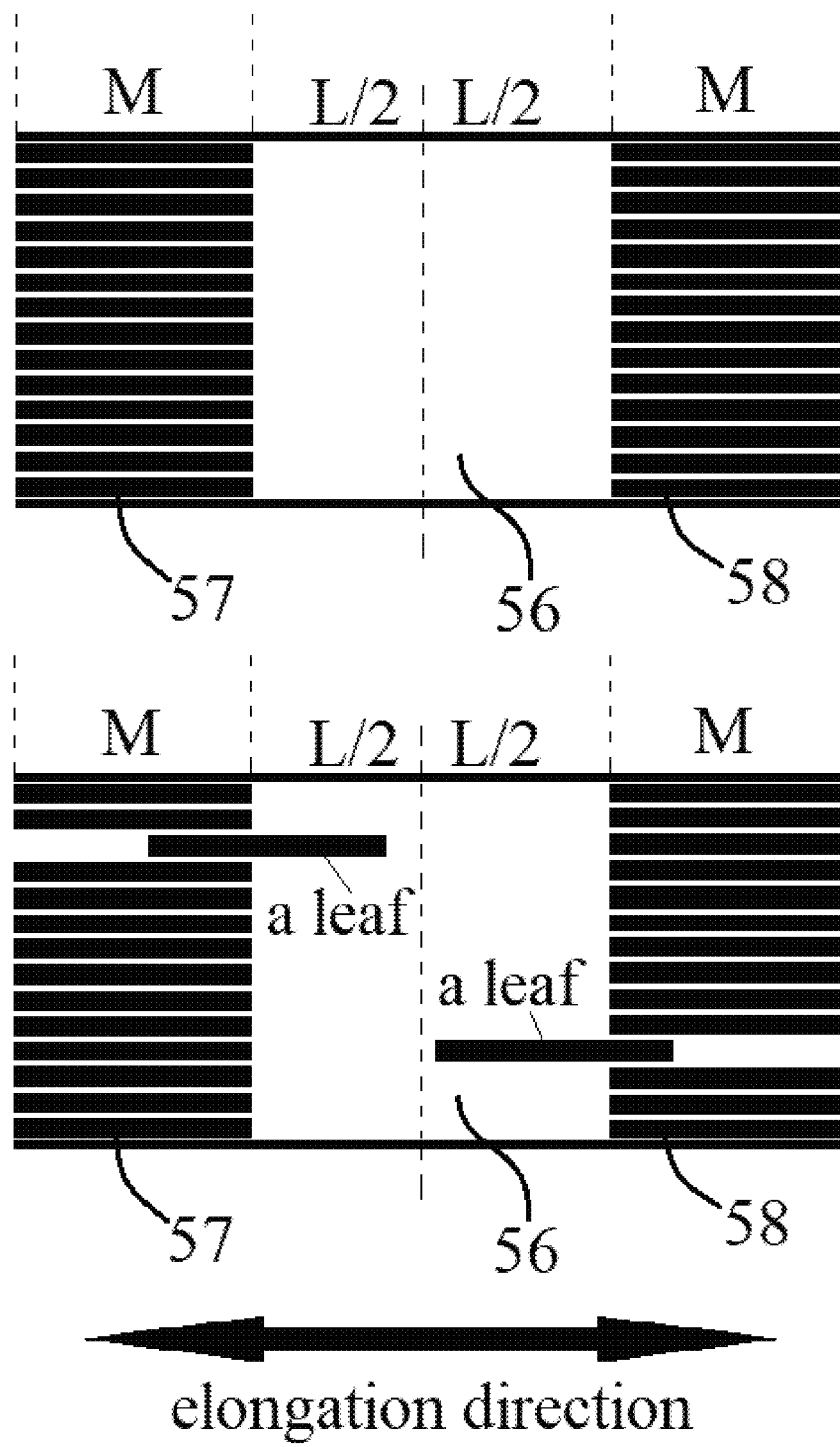
FIG. 13 schematically shows a compact MLC designed for the radiotherapeutical or radiosurgical system in accordance with an exemplary embodiment of the present invention.

Therefore, in some radiotherapeutical or radiosurgical systems of the invention, a special multi-leave collimator (MLC) (12, 23, and 33) as shown in FIG. 13 is provided for each radiation source. Each MLC includes two arrays (57, 58) of movable and parallel leaves with a gap 56 between the two arrays (57, 58). Each leaf in the two arrays of leaves (57, 58) can independently of each other protrude or travel into the gap 56 along an elongation direction of said leaf. The gap 56 has a length of L along the elongation direction, and each leaf in the two arrays (57, 58) has a length of M along the elongation direction. In various embodiments, 0.5 L<M<0.6 L such as 0.51 L<M<0.56 L or 0.52 L<M<0.54 L. The height of the gap 56 may be the same as L (as in a square opening) or longer/shorter than L (as in a rectangular opening). With such a MLC design, each leaf only needs to protrude (or travel) a maximal distance of L/2 toward the middle line of the gap 56 (or a radiation field), instead of traveling a maximal distance of L toward the middle line, i.e. all the way to the opposite end of the gap 56 (or an opening). As such, the leave length M is significantly reduced from greater than L in the prior art down to e.g. less than 0.6 L in the present embodiments. The overall dimension of the MLC (12, 23, and 33), and consequently the dimension of treatment unit 4, is also reduced accordingly.

Some operations, tasks, and functions of the radiotherapeutical or radiosurgical treatment method according to the present invention may be computer-executed, computerized, processor-executed, software-implemented, or computer-implemented with hardware, software, firmware, or any combination thereof. When implemented in software or firmware, various elements of the systems/method described herein are essentially the code segments or executable instructions that, when executed by one or more processor devices, cause the host computing system to perform the various tasks. In certain embodiments, the program or code segments are stored in a tangible processor-readable medium, which may include any medium that can store or transfer information. Examples of suitable forms of non-transitory and processor-readable media include an electronic circuit, a semiconductor memory device, a ROM, a flash memory, an erasable ROM (EROM), a floppy diskette, a CD-ROM, an optical disk, a hard disk, or the like.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A radiotherapeutical or radiosurgical system comprising:

at least two radiation sources configured to rotate around a common rotation axis and to target at or aim at a common point on the common rotation axis;

wherein the common point on the common rotation axis is defined as an isocenter, and a predetermined treatment target is located at the isocenter;

wherein a first radiation source of said at least two radiation sources emits a first radiation beam, which irradiates upon the predetermined treatment target from a first direction along a central axis of the first radiation beam, and a first angle $\alpha1$ is defined as an angle between the first direction and the common rotation axis;

wherein a second radiation source of said at least two radiation sources emits a second radiation beam, which irradiates upon the predetermined treatment target from a second direction along a central axis of the second radiation beam, and a second angle $\alpha2$ is defined as an angle between the second direction and the common rotation axis;

wherein, when said at least two radiation sources are rotating around the common rotation axis, the first angle $\alpha1$ and the second angle $\alpha2$ are independently of each other constant or being varied or being changed;

wherein, when the first angle $\alpha1$ and the second angle $\alpha2$ are independently of each other being varied or being changed, the first angle $\alpha1$ and/or the second angle $\alpha2$ is/are being varied or being changed within a magnitude of less than ±15° of initial values of the first angle $\alpha1$ and/or the second angle $\alpha2$ before said at least two radiation sources start to rotate around the common rotation axis;

wherein, when said at least two radiation sources are rotating around the common rotation axis, it always remains that at least $\alpha1 \neq \alpha2$, regardless whether the first angle $\alpha1$ and the second angle $\alpha2$ are independently of each other constant or being varied or being changed; and wherein the at least two radiation sources comprise linear accelerators (LINACs) or other compact radiation sources that have a dose rate at least higher than 3 Gy/minute in a 100-cm source-to-predetermined treatment target distance for each source of said at least two radiation sources.

2. The radiotherapeutical or radiosurgical system according to claim 1, wherein said at least two radiation sources include at least three radiation sources comprising a third radiation source that is also configured to rotate around the common rotation axis and to target at or to aim at the common point on the common rotation axis;

wherein the third radiation source emits a third radiation beam, which irradiates upon the predetermined treatment target from a third direction along a central axis of the third radiation beam, and a third angle $\alpha3$ is defined as an angle between the third direction and the common rotation axis;

wherein, when the at least three radiation sources are rotating around the common rotation axis, the first angle $\alpha1$, the second angle $\alpha2$, and the third angle $\alpha3$ are independently of each other constant or being varied or being changed; wherein, when the first angle $\alpha1$, the second angle $\alpha2$ and the third angle $\alpha3$ are independently of each other being varied or being changed, the first angle $\alpha1$, the second angle $\alpha2$, and/or the third angle $\alpha3$ is/are being varied or being changed within a magnitude of less than ±15° of initial values of the first angle $\alpha1$, the second angle $\alpha2$, and/or the third angle α3 before said at least three radiation sources start to rotate around the common rotation axis; and wherein, when the at least three radiation sources are rotating around the common rotation axis, it always remains that at least α1≠α2, α1≠α3, and α2≠α3, regardless whether the first angle α1, the second angle α2, and the third angle α3 are independently of each other constant or being varied or being changed.

3. The radiotherapeutical or radiosurgical system according to claim 2, wherein an initial value of the first angle α1 is in a range of 30-75°, an initial value of the second angle α2 is in a range of 75-105°, and an initial value of the third angle α3 is in a range of 105-150°, before said at least three radiation sources start to rotate around the common rotation axis.

4. The radiotherapeutical or radiosurgical system according to claim 2, wherein each of said at least three radiation sources projects onto a plane passing through the isocenter and perpendicular to the common rotation axis, and a line connecting a projection spot of one of said at least three radiation sources on the plane and the isocenter is defined as a projection line of a corresponding radiation source of said at least three radiation sources;

wherein an angle β1 is defined as an angle between a projection line of the first radiation source and a projection line of the second radiation source;

wherein an angle β2 is defined as an angle between the projection line of the second radiation source and a projection line of the third radiation source;

wherein an angle β3 is defined as an angle between the projection line of the third radiation source and the projection line of the first radiation source; and wherein the angle β1, the angle β2, and the angle β3 are independently of each other in a range of 100-140°.

5. The radiotherapeutical or radiosurgical system according to claim 4, wherein the at least three radiation sources comprise only three radiation sources, and wherein β1=β2=β3=120°.

6. The radiotherapeutical or radiosurgical system according to claim 2, wherein said at least three radiation sources are able to deliver at least 3 non-coplanar arcs, which are equivalent to 360° non-coplanar radiation beams toward the isocenter if a 3° span of a rotation angle is considered as a different beam for said at least three radiation sources in a single 360° rotation around the common rotation axis.

7. The radiotherapeutical or radiosurgical system according to claim 1, wherein initial values of the first angle α1 and the second angle α2 are allowed to be adjusted for an individual patient before said at least two radiation sources start to rotate around the common rotation axis.

8. The radiotherapeutical or radiosurgical system according to claim 1, further comprising a ring-shaped imaging device for determining a target within a patient's body as said predetermined treatment target, and for guiding radiation beams to focus on or aim at said predetermined treatment target.

9. The radiotherapeutical or radiosurgical system according to claim 8, wherein the ring-shaped imaging device comprises a CT, an MRI, a PET, or any combinations thereof.

10. The radiotherapeutical or radiosurgical system according to claim 1, wherein the LINACs have an energy of <8 MeV, or a length of the linear accelerators is less than 80 cm, and the LINACs do not comprise bending magnets; and wherein the first direction and the second direction are the same as an axis of accelerator tubes of the LINACs.

11. The radiotherapeutical or radiosurgical system according to claim 1, wherein the LINACs have an energy of >8 MeV, or a length of the linear accelerator is longer than 40 cm, and the LINACs do not comprise bending magnets; and wherein the first direction and the second direction are different from an axis of accelerator tubes of the LINACs.

12. The radiotherapeutical or radiosurgical system according to claim 1, further comprising a multi-leaf collimator (MLC) for each radiation source of the at least two radiation sources, wherein each MLC includes two arrays of movable and parallel leaves with a gap between the two arrays;

wherein each leaf in the two arrays of movable and parallel leaves can independently of each other protrude or travel into the gap along an elongation direction of each leaf;

wherein the gap has a length of L along the elongation direction, and each leaf in the two arrays of movable and parallel leaves has a length of M along the elongation direction; and wherein 0.5L<M<0.6L.

13. The radiotherapeutical or radiosurgical system according to claim 12, wherein the multi-leaf collimator shapes a radiation field to conform with a target shape in a beam's eye view, and changes a field shape during a rotation because the target shape in the beam's eye view changes with different beam directions; and wherein a use of the multi-leaf collimator to change a shape of a radiation field during a rotation according to a change of a target shape in a beam's eye view can improve an efficiency of radiation treatment planning and a radiation treatment delivery.

14. The radiotherapeutical or radiosurgical system according to claim 1, wherein the LINACs can be modulated for their radiation output or dose rate during a radiation delivery.

15. The radiotherapeutical or radiosurgical system according to claim 14, wherein a dose rate from a LINAC is temporarily reduced to 0-90% of a standard dose rate when the LINAC rotates around the common rotation axis to a degree that a critical organ under a protection is seen from a beam's eye view; and wherein such a modulation of an intensity or a dose rate allows a reduction of a radiation dose to the critical organ to a satisfaction level.

16. A radiotherapeutical or radiosurgical treatment method comprising:
  (i) providing the radiotherapeutical or radiosurgical system of claim 1;
  (ii) providing a system of treatment planning, wherein a predetermined treatment target is contoured in a 3-dimensional (3D) imaging set, and a dose rate and a collimator shape of each radiation source of the at least two radiation sources at each ration angle in a 360° rotation are determined according to a dose prescription and a target shape in each beam's eye view;
  (iii) positioning a patient according to the 3D imaging set as provided by a ring-shaped imaging device so that the predetermined treatment target is in exactly the same position as that in the 3D imaging set in the system of treatment planning; and
  (iv) delivering a prescription radiation dose to the predetermined treatment target according to a treatment plan and completing a treatment within 0.1-20 seconds in a full 360° rotation, a partial rotation with any angle less than 360°, or no rotation.

17. The radiotheraputical or radiosurgical treatment method according to claim 16, further comprising calculating a treatment delivery time or a rotation time based on a maximal dose rate of each radiation source of the at least two radiation sources, a maximal rotation speed, and a prescription dose.

18. The radiotheraputical or radiosurgical treatment method according to claim 16, further comprising:
utilizing multi-leaf collimators to conform a change of the target shape during a source rotation,
utilizing multiple high-dose-rate radiation sources as said at least two radiation sources to increase the dose rate, and
reducing a treatment delivery time to less than 20 seconds for any shapes and sizes of a tumor, over a conventional gamma knife and Zap-X devices, which all use circular collimators, and whose treatment delivery time is often more than 30 minutes for large tumors.

\* \* \* \* \*